(12) United States Patent
Molloy et al.

(10) Patent No.: US 11,964,172 B2
(45) Date of Patent: *Apr. 23, 2024

(54) QUALITY ASSURANCE DEVICE FOR A MEDICAL ACCELERATOR

(71) Applicant: University of Kentucky Research Foundation, Lexington, KY (US)

(72) Inventors: Janelle A. Molloy, Lexington, KY (US); Dennis A. Cheek, Lexington, KY (US); Quan Chen, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 245 days.

This patent is subject to a terminal disclaimer.

(21) Appl. No.: 17/420,659

(22) PCT Filed: Dec. 12, 2019

(86) PCT No.: PCT/US2019/066007
§ 371 (c)(1),
(2) Date: Jul. 2, 2021

(87) PCT Pub. No.: WO2020/146086
PCT Pub. Date: Jul. 16, 2020

(65) Prior Publication Data
US 2022/0096868 A1 Mar. 31, 2022

Related U.S. Application Data

(60) Provisional application No. 62/789,196, filed on Jan. 7, 2019.

(51) Int. Cl.
*A61N 5/10* (2006.01)
*H05H 7/02* (2006.01)

(52) U.S. Cl.
CPC .......... *A61N 5/1075* (2013.01); *A61N 5/1048* (2013.01); *H05H 7/02* (2013.01); *A61N 2005/1076* (2013.01)

(58) Field of Classification Search
CPC ............... A61N 5/1048; A61N 5/1075; A61N 2005/1076; H05H 7/02
See application file for complete search history.

(56) References Cited

U.S. PATENT DOCUMENTS 9,211,101 B2  12/2015  Wong et al.
2002/0181660 A1*  12/2002  Reinstein ............. A61N 5/1048
                                                        378/207

(Continued)

FOREIGN PATENT DOCUMENTS

JP    2011053037 A     3/2011
WO   WO2016081622 A1  5/2016
WO   WO2016148269 A1  9/2016

*Primary Examiner* — Blake C Riddick
(74) *Attorney, Agent, or Firm* — Stites & Harbison PLLC; Warren D. Schickli

(57) ABSTRACT

A quality assurance device for a medical accelerator includes a housing having an inner radioluminescent layer adapted to provide a visual indication when contacted with invisible radiation generated by the medical accelerator. In addition, the quality assurance device includes one or more cameras located within the housing and adapted to image the inner radioluminescent layer of the housing including the visual indication.

10 Claims, 6 Drawing Sheets

(56) References Cited

U.S. PATENT DOCUMENTS

| | | | | |
|---|---|---|---|---|
| 2007/0071176 | A1* | 3/2007 | Main | A61N 5/1075 |
| | | | | 378/207 |
| 2008/0069303 | A1* | 3/2008 | Kim | A61N 5/1048 |
| | | | | 378/98.2 |
| 2008/0240364 | A1* | 10/2008 | Main | A61N 5/1048 |
| | | | | 250/252.1 |
| 2010/0097293 | A1 | 4/2010 | McMahon | |
| 2014/0267697 | A1* | 9/2014 | Wong | A61B 6/4216 |
| | | | | 348/135 |
| 2015/0035942 | A1* | 2/2015 | Hampton | A61N 5/1049 |
| | | | | 348/42 |
| 2015/0036806 | A1* | 2/2015 | Wong | A61N 5/1075 |
| | | | | 378/207 |
| 2015/0085993 | A1* | 3/2015 | Scheib | A61N 5/1071 |
| | | | | 378/207 |
| 2015/0343240 | A1* | 12/2015 | Beaumont | A61N 5/1075 |
| | | | | 378/207 |
| 2015/0343241 | A1* | 12/2015 | Han | G06T 5/003 |
| | | | | 378/205 |
| 2015/0360056 | A1* | 12/2015 | Xing | A61N 5/1075 |
| | | | | 250/362 |
| 2017/0128750 | A1* | 5/2017 | Filiberti | A61N 5/1045 |
| 2017/0197091 | A1* | 7/2017 | Ju | A61N 5/1064 |
| 2017/0312547 | A1* | 11/2017 | Wong | A61N 5/1082 |
| 2017/0347987 | A1 | 12/2017 | Hong et al. | |
| 2018/0318609 | A1* | 11/2018 | Arican | A61N 5/1075 |
| 2019/0255358 | A1* | 8/2019 | Hale | A61N 5/1045 |

\* cited by examiner

QUALITY ASSURANCE DEVICE FOR A MEDICAL ACCELERATOR

RELATED APPLICATIONS

This application is a national stage application, filed under 35 U.S.C. § 371, of International Patent Application No. PCT/US2019/066007 filed Dec. 12, 2019, which claims priority to U.S. Provisional Application 62/789,196 filed Jan. 7, 2019, which is hereby incorporated by reference in its entirety.

TECHNICAL FIELD

This document relates generally to the medical equipment field and, more particularly, to a quality assurance device adapted for calibrating and verifying proper operation of a medical accelerator.

BACKGROUND

This document relates generally to a new and improved quality assurance device adapted for acquiring quality assurance measurements on medical linear accelerators used for radiation therapy of cancer patients. The quality assurance device is designed so that it is capable of acquiring comprehensive optical, radiation and dosimetric data required by the American Association of Physicists in Medicine Task Group 142 Report (AAPMTG 142 dated 2009) daily and monthly QA protocols. In addition, the quality assurance device is designed such that it may be used to acquire patient-specific QA data, including for patients being treated with intensity modulated radiation therapy (IMRT QA) and volume modulated arc therapy (VMAT) as well as any other modulated, or non-modulated treatment modality.

SUMMARY

In accordance with the purposes and benefits described herein, a new and improved quality assurance device is provided for a medical accelerator. That quality assurance device comprises (a) a housing having an inner radioluminescent layer adapted to provide a visual indication when contacted with invisible radiation generated by the medical accelerator and (b) at least one camera, located within the housing, adapted to image the inner radioluminescent layer of the housing including the visual indication.

In one or more of the many possible embodiments of the quality assurance device, the quality assurance device includes a radiation detector located within the housing. In one or more of the many possible embodiments of the quality assurance device, the quality assurance device includes a calibrated light source located within the housing. In one or more embodiments of the quality assurance device, the quality assurance device further includes at least one imaging test object carried on the housing.

The at least one imaging test object may include a first group of imaging test objects positioned on a side of the housing and adapted to evaluate diagnostic, kV image quality including spatial resolution, contrast resolution and geometric integrity. In one or more of the many possible embodiments, the at least one imaging test object may include a second group of imaging test objects positioned on a side of the housing (the side facing down when positioned on a treatment couch when completing quality assurance testing of a medical accelerator) and adapted to evaluate mega-voltage (MV) image quality of an electronic portal imaging device (EPID) of the medical accelerator including spatial resolution, contrast resolution and geometric integrity. Further, the at least one imaging test object may include a computed tomography or CT image quality phantom on a superior side closest to an accelerator gantry of the medical accelerator during quality assurance testing. That CT image quality phantom may include a radioluminescent phosphor on one side visible to the at least one camera. Further, the CT image quality phantom may further include a radiation dose detector.

The housing of the quality assurance device may include an outer layer of semitransparent material. In one or more of the many possible embodiments of the quality assurance device, the housing may include an outer layer of switchable material having a first state wherein visible light passes through the switchable material and a second state wherein visible light is at least partially obstructed from passing through the switchable material.

In one or more of the many possible embodiments of the quality assurance device, the quality assurance device may include a plurality of receivers within the housing. The at least one camera may be held on a first insert adapted to be releasably received by at least one of the plurality of receivers. This allows for easy installation, maintenance and repair of the at least one camera within the housing of the quality assurance device.

In one or more of the many possible embodiments, the radiation detector of the quality assurance device may be held on a second insert also adapted to be releasably received by at least one of the plurality of receivers. Once again, this allows for easy installation, maintenance and repair of the radiation detector.

In accordance with yet an additional aspect, the quality assurance device may further include a computing device. That computing device may be configured to convert light intensity detected by the at least one camera to radiation dose. That computing device may be configured to convert light intensity detected by the at least one camera to radiation fluence. That computing device may be configured to convert spatial location of the visual indication on the inner radioluminescent layer to a coordinate system that is defined relative to the medical accelerator. That computing device may be configured to compare locations of the radiation and radiation boundaries to the locations indicated by sources of visible light including room lasers, a medical accelerator light field and medical accelerator crosshairs associated with the medical accelerator and adapted to aid in the targeting of the radiation delivered by the medical accelerator. Further, the computing device may also be configured to receive readings or data from the radiation detector and/or the calibrated light source and analyze those readings relative to expected values.

In accordance with an additional aspect, a method of quality assurance for a medical accelerator is provided. That method may be broadly described as comprising the steps of: (a) positioning a quality assurance device on a treatment couch of the medical accelerator and (b) detecting the radiation delivered by the medical accelerator to the quality assurance device by producing a visual indication of the radiation on an inner layer of the housing of the quality assurance device and imaging that visual indication with at least one camera located within the housing of the quality assurance device. Still further, the method may include the step of switching a switchable material, on an outer layer of the housing, into a first state wherein visible light passes through the switchable material when the quality assurance device is positioned on the treatment couch. This aids the operator in properly positioning the quality assurance device on the treatment couch for the purpose of calibrating and verifying the proper operation of the medical accelerator. Further, the method may include the step of switching the switchable material into a second state, wherein visible light is at least partially obstructed from passing through the switchable material, when the radiation delivered by the medical accelerator is being detected. This serves to reduce or eliminate ambient light from the exterior of the housing which might otherwise interfere with or degrade the ability to accurately detect the visual indication of the radiation provided on the inner layer of the housing and thereby interfere with calibration and verification of the proper operation of the medical accelerator.

Advantageously, the quality assurance device and the related method of quality assurance for a medical accelerator are easy to utilize and allow one to quickly and efficiently calibrate and verify the proper operation of a medical accelerator in accordance with substantially any foreseeable daily and monthly quality assurance protocols that might be in effect for the medical accelerator being tested.

In the following description, there are shown and described several preferred embodiments of the quality assurance device as well as the related method of quality assurance for a medical accelerator. As it should be realized, the quality assurance device and method are capable of other, different embodiments and their several details are capable of modification in various, obvious aspects all without departing from the quality assurance device and method as set forth and described in the following claims. Accordingly, the drawings and descriptions should be regarded as illustrative in nature and not as restrictive.

BRIEF DESCRIPTION OF THE DRAWING FIGURES

The accompanying drawing figures incorporated herein and forming a part of the specification, illustrate several aspects of the quality assurance device and the related method and together with the description serve to explain certain principles thereof.

Reference will now be made in detail to the present preferred embodiments of the quality assurance device, examples of which are illustrated in the accompanying drawing figures.

DETAILED DESCRIPTION

Figure 1:
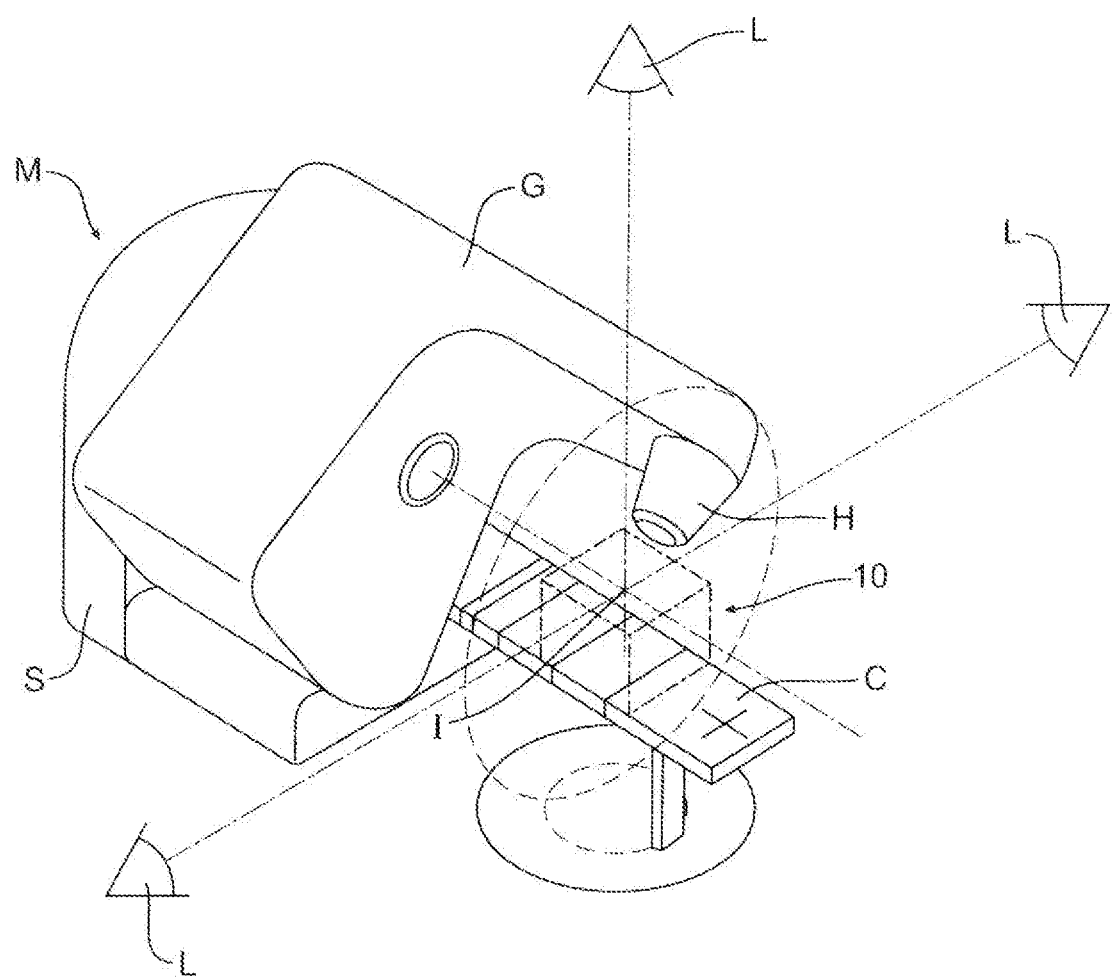
FIG. 1 is a perspective view of a medical accelerator that illustrates the quality assurance device positioned on the treatment couch, at the intersection of the room lasers, adjacent the gantry of the medical accelerator.

Reference is now made to FIG. 1 illustrating the new and improved quality assurance device 10 and a medical accelerator M. As illustrated, the medical accelerator M includes a gantry G supported for rotation with respect to a stand S. A treatment head H carried on the gantry G directs radiation toward a target located at the isocentre I. Room lasers L function to identify the isocentre I. As illustrated in FIG. 1, the quality assurance device 10 has been positioned on the treatment couch C of the medical accelerator M at the isocentre I using the room lasers L as a guide.

Figure 2:
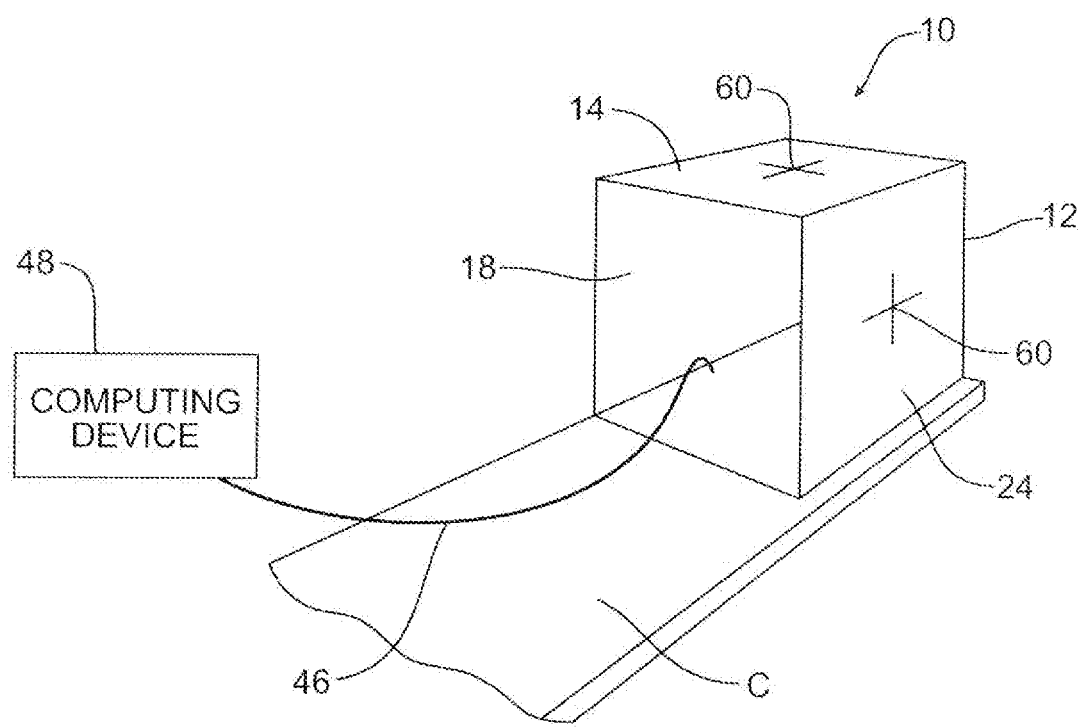
FIG. 2 is a detailed perspective view illustrating a quality assurance device including the housing and the electrical/communications cable protruding from the housing and connecting the electronic components contained in the housing to the computing device that controls the operation of the quality assurance device.
Figure 3:
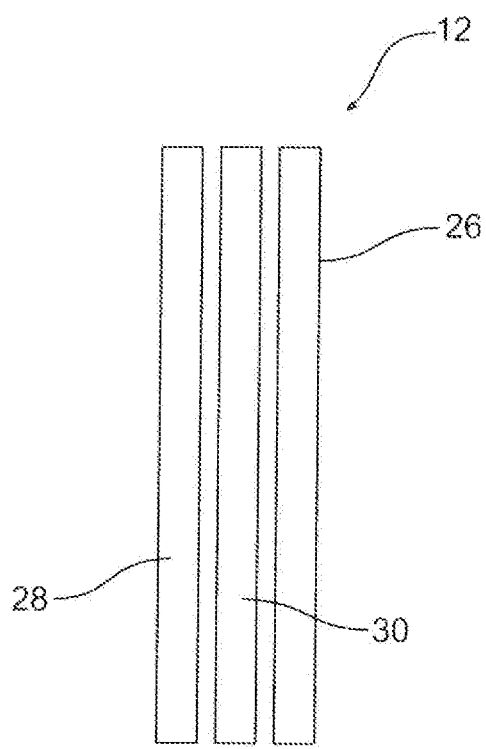
FIG. 3 is a schematic illustration of the construction of the housing including the inner scintillation layer, the outer switchable material layer and the intermediate mechanical layer for structural integrity.

Reference is now made to FIGS. 2-6 which when considered together illustrate the structure of the quality assurance device 10. As shown, the quality assurance device 10 comprises a housing 12. In the illustrated embodiment, the housing 12 has the overall shape of a cube including six sides 14, 16, 18, 20, 22 and 24. When positioned on the treatment couch C to perform quality assurance testing of the medical accelerator M, the side 14 faces up, the side 16 faces down toward the treatment couch and the side 22 is oriented toward the gantry G. As illustrated in FIG. 3, each side 14, 16, 18, 20, 22, 24 includes an inner scintillation or radioluminescent layer 26, an outer layer 28 made from a semitransparent or switchable material and an intermediate structural layer 30 to provide strength and rigidity.

More particularly, the inner radioluminescent layer 26 is adapted to provide a visual indication when contacted with invisible radiation generate by the medical accelerator M. The outer layer 28 may be made from a semitransparent material. In one or more of the many possible embodiments of the quality assurance device 10, the outer layer 28 is made from a switchable material of a type known in the art having a first state wherein visible light passes through the switchable material and a second state wherein visible light is at least partially and in some embodiments totally obstructed from passing through the switchable material.

Figure 4:
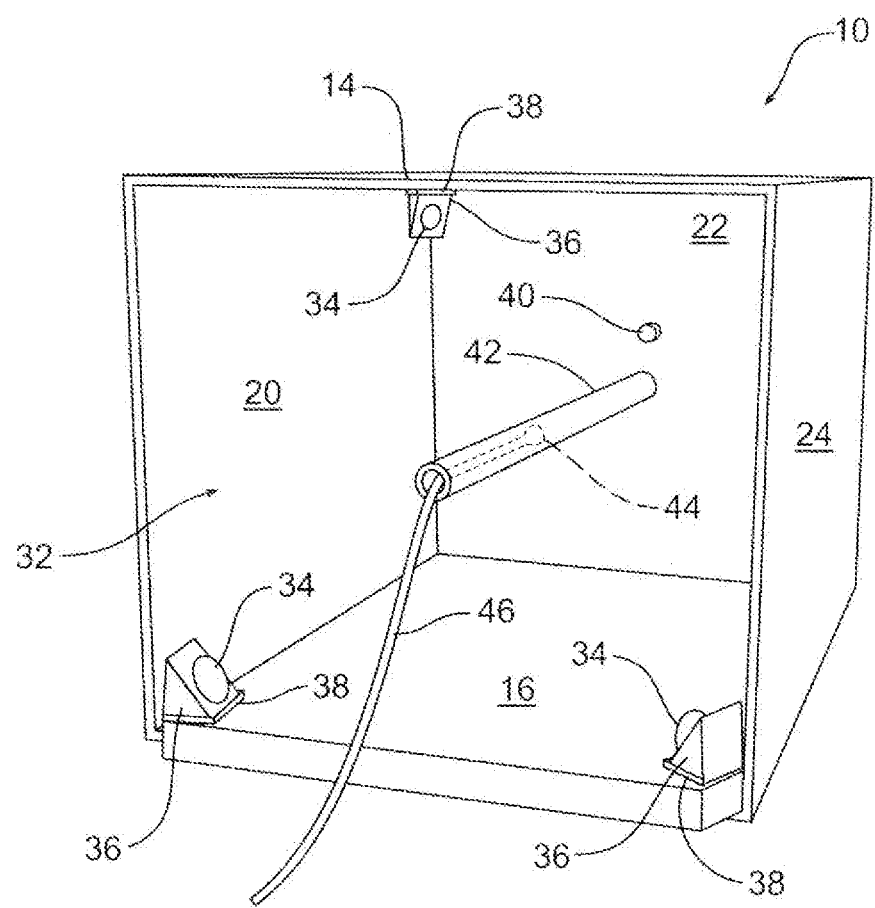
FIG. 4 is a perspective view of the quality assurance device with a sidewall of the housing removed to illustrate three cameras and an integrated radiation detector held in inserts within the housing.

FIG. 4 illustrates the quality assurance device 10 with a side 18 removed to illustrate the interior 32 of the quality assurance device 10. In the illustrated embodiment, three cameras 34 are held in inserts 36 that may be removably mounted in receivers 38 at three corners of the housing 12. As will be described in greater detail below, these cameras 34 are adapted to image the inner radioluminescent layer 26 of the housing 12 including the visual indication that is produced when the inner radioluminescent layer 26 is contacted with invisible radiation generated by the medical accelerator M.

As further illustrated in FIG. 4, an optional calibrated light source 40 is located within the housing 12. In the illustrated embodiment that calibrated light source 40 is illustrated positioned on the inner surface of the side 22.

As further illustrated in FIG. 4, a removable support tube 42 is also mounted to the side 22. A radiation detector 44 is located within the housing carried by or embedded in the support tube 42. An electrical/communications cable 46 protrudes through the side 18 (see also FIG. 2) and functions to connect the various electronic devices within the housing 12 including the cameras 34, calibrated light source 40 and radiation detector 44 with a computing device 48 located outside of the housing 12. That computing device 48 may comprise one or more processors, one or more memories and one or more network interfaces all in communication with each other over a communication bus. In one or more embodiments, the computing device 48 may comprise a dedicated microprocessor or an electronic control unit (ECU) operating in accordance with instructions from appropriate control software.

The computing device 48 may be adapted or configured to (a) convert light intensity detected by at least one camera 34 to radiation dose delivered by the medical accelerator M, (b) convert light intensity detected by the at least one camera 34 to radiation fluence of the medical accelerator, (c) convert spatial location of the visual indication on the inner radioluminescent layer 26 to a coordinate system that is defined relative to the medical accelerator and (d) compare locations of the radiation and radiation boundaries to the locations indicated by sources of visible light including, for example, the room lasers L, any medical accelerator light field and any medical accelerator crosshairs associated with the medical accelerator M being tested for quality assurance utilizing the quality assurance device 10. The computing device 48 may also be configured to receive signals from either or both of the calibrated light source and the removable radiation detector and acquire or interpret data coming from those components.

Figure 5:
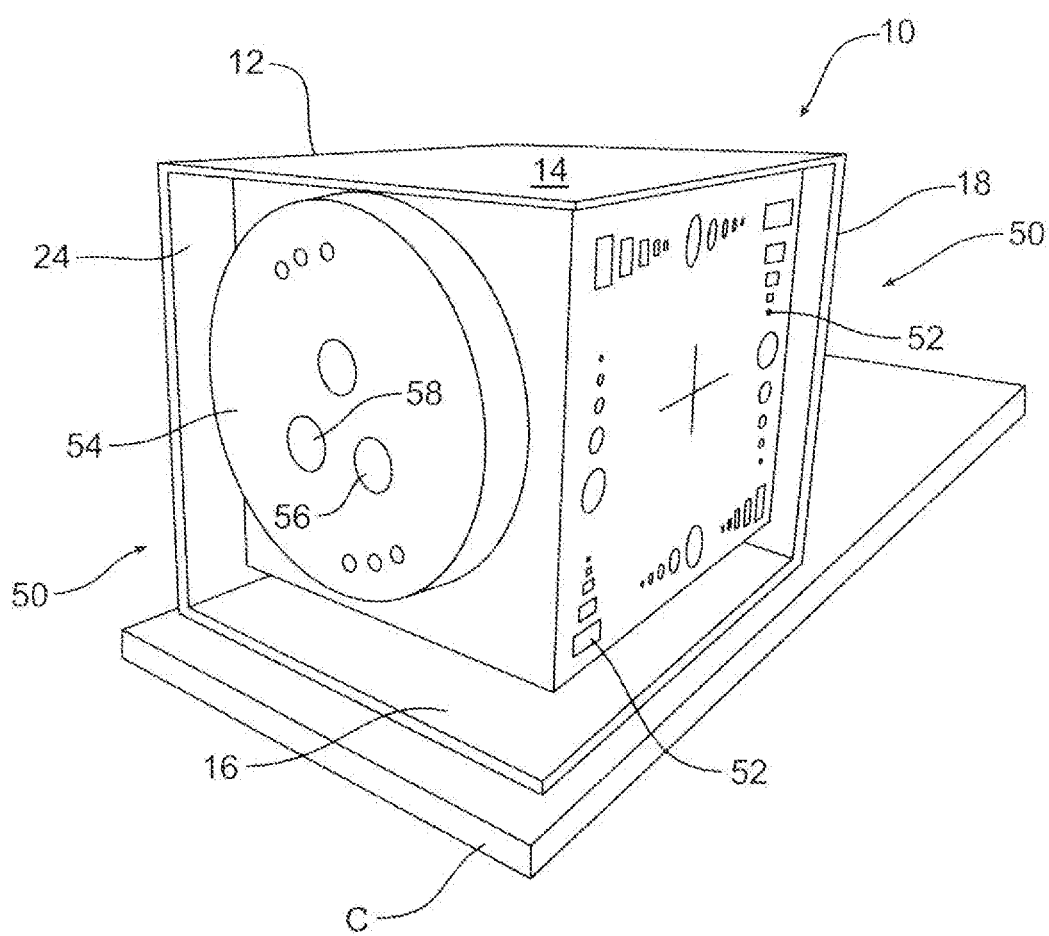
FIG. 5 is a perspective view of the quality assurance device illustrating a CT image quality phantom on a superior side of the housing located closest to the gantry of the medical accelerator and a first group of imaging test objects on an adjacent side of the housing.
Figure 6:
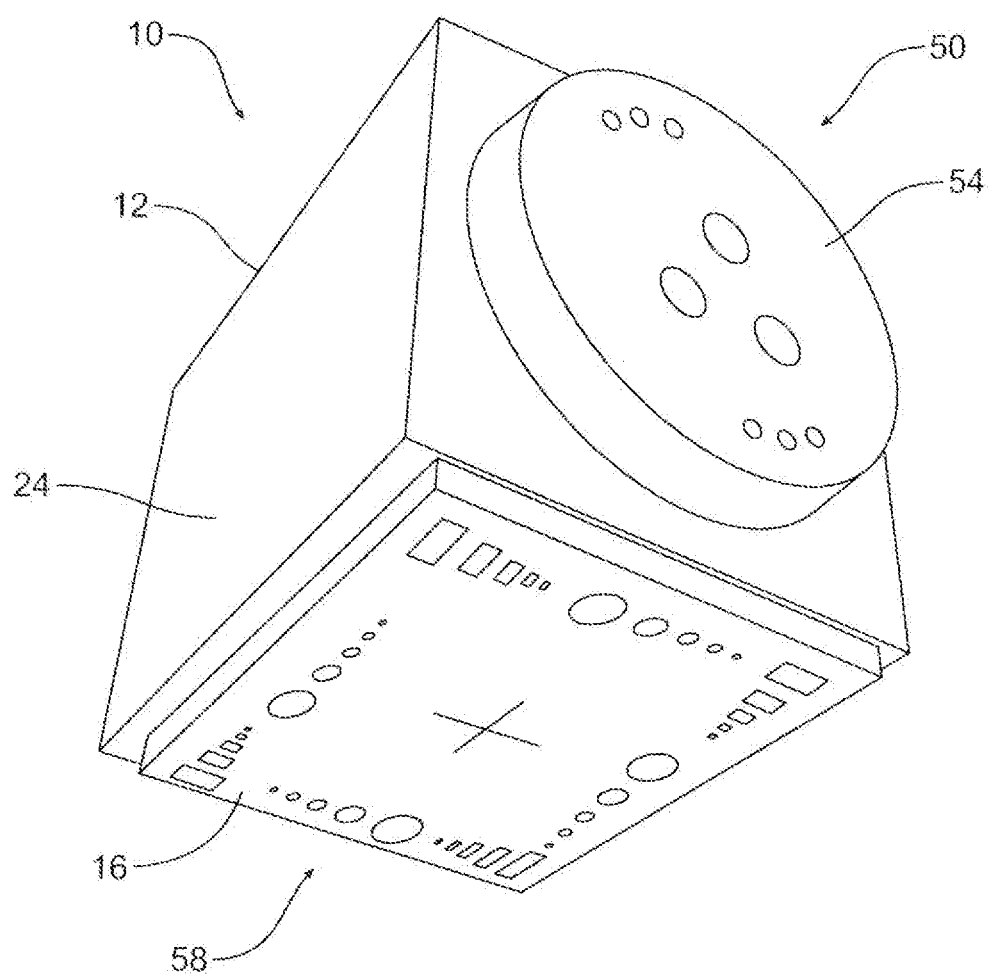
FIG. 6 is a perspective view of the bottom of the quality assurance device with the lower wall removed and illustrating the second group of imaging test objects adjacent the lower surface of the housing.

As illustrated in FIGS. 5 and 6, the quality assurance device 10 further includes at least one imaging test object 50 carried on the housing 12. That at least one imaging test object 50 may include a first group 52 positioned along a side, such as the side 20 of the housing 12. The first group of imaging test objects 52 are adapted to evaluate diagnostic, kV image quality including spatial resolution, contrast resolution and geometric integrity. As further illustrated in FIG. 5, the at least one imaging test object 50 may also include a CT image quality phantom 54 on the side 22 which is oriented toward and closest to the accelerator gantry G of the medical accelerator M when the quality assurance device 10 is positioned for testing. More particularly, the CT image quality phantom 54 may include a radioluminescent phosphor 56 on one side visible to at least one of the cameras 34 and a radiation dose detector 58.

As illustrated in FIG. 6, the at least one imaging test object 50 may also include a second group of imaging test objects 58 positioned on the side 16 which faces down toward the treatment couch C when the quality assurance device 10 is positioned for testing. The second group of imaging test objects 58 is adapted to evaluate mega-voltage (MV) image quality of an electronic portal imaging device (EPID) of the medical accelerator M including spatial resolution, contrast resolution and geometric integrity.

The quality assurance device 10 illustrated in FIGS. 1-6 is useful in a method of quality assurance for a medical accelerator M. That method includes the step of positioning the quality assurance device 10 on the treatment couch C of the medical accelerator M. More particularly, as illustrated in FIGS. 1 and 2, the quality assurance device 10 is positioned on the treatment couch C with the assistance of the room lasers L and crosshair alignment indicia 60 provided on the exterior of one or more sides 14, 16, 18, 20, 22, 24 of the housing 12. This ensures that the quality assurance device 10 is properly positioned with respect to the isocentre I of the medical accelerator M. During the positioning of the quality assurance device 10 on the treatment couch C, the switchable material on the outer layer 28 of the housing 12 may be switched into a first state wherein visible light passes through the switchable material. This further aids in the positioning of the device 10. Note also that the quality assurance device is positioned with the side 14 oriented upward, the side 16 oriented downward and the side 22 oriented toward the gantry G.

Once the quality assurance device 10 has been properly positioned on the treatment couch C, the method includes switching the switchable material into a second state wherein visible light is at least partially obstructed from passing through the switchable material. This either diminishes or eliminates ambient room lighting from passing through the housing 12 into the interior 32 of the housing where such light can interfere with detection of the visual indication of the radiation that is produced or generated when the invisible radiation generated by the medical accelerator M impinges upon the inner radioluminescent layer 26 of the housing 12.

The method also includes the step of detecting the radiation delivered by the medical accelerator M to the quality assurance device 10. As noted, that radiation produces a visual indication on the inner layer 26 of the housing 12 of the quality assurance device 10. Toward this end, the method includes imaging that visual indication with the camera or cameras 34 located within the housing 12 of the quality assurance device 10. The image of that visual indication is then communicated through the electrical/communication cable 46 to the computing device 48 which has been adapted or configured to: (a) convert light intensity detected by the camera or cameras 34 to radiation dose, (b) convert light intensity detected by the at least one camera to radiation fluence, (c) convert spatial location of the visual indication on the inner radioluminescent layer 26 to a coordinate system as defined relative to the medical accelerator M and (d) compare locations of the radiation and radiation boundaries to the locations indicated by sources of visible light including the room lasers L, a medical accelerator light field and any medical accelerator crosshairs associated with the medical accelerator. In this way it is possible to properly calibrate and ensure optimization of function of the medical accelerator M in a simple and efficient manner. Still further, the method may also include the steps of receiving signals from either or both of the calibrated light source and the removable radiation detector and acquiring or interpreting data coming from those components.

A number of benefits and advantages are associated with the quality assurance device 10 as well as the method of quality assurance for a medical accelerator M. The positioning of the camera or cameras 34 within the housing 12 allows for a more compact quality assurance device 10 having a smaller form factor and also allows for the acquisition of more data with fewer cameras as well as for the acquisition of data without having to reposition the cameras during operation of the medical accelerator M and rotation of the gantry G.

The use of the switchable material or switchable glass for the outer layer 28 of the housing 12 allows for the exclusion of ambient room light from the interior 32 of the housing 12. This allows the camera or cameras 34 to detect smaller changes in the visual indications of the radiation and thus in radiation dose and, thereby, allows for the collection of higher quality data.

At the same time, when the switchable material of the outer layer 28 is in a first state during positioning of the quality assurance device 10 on the treatment couch C, visible room light including positioning markers from the room lasers L, any medical accelerator light field and medical accelerator crosshairs allow the cameras to uniquely record the positioning of the quality assurance device 10 relative to these external positioning features.

By integrating the imaging test objects 50, including the first group of test objects 52, the CT image quality phantom 54 and the second group of test objects 58 into the housing 12 of the quality assurance device 10 all TG 142 monthly compliance data may be acquired utilizing the quality assurance device 10 with minimal operator intervention.

The placement or positioning of the first group of imaging test objects 52 on the side 20 of the housing 12 and the second group of imaging test objects 58 on the lower side 16 of the housing 12 means that the gantry G on the majority of "conventional" medical accelerators M does not need to be rotated for the kV and MV image tests. This saves trips in and out of the treatment vault and thus time for data collection. The switchable material/switchable glass feature of the outer layer 28 of the housing 12 enables ambient room light to be excluded without the operator having to enter the room and place or remove a cover and thus also saves time and contributes to the efficiency in using the quality assurance device 10.

The quality assurance device 10 and the related method described herein allow the acquisition of comprehensive TG 142 data in 30 minutes or less with a minimum of operator intervention. The ease of use and automation provided by the quality assurance device 10 and related method is such that the quality assurance procedure can be completed by technicians as well as qualified medical physicists.

Data from the integrated radiation detector 44 can be electronically read by the computing device 48 and uploaded to a centralized data repository. The data readings can be compared to other clinics' data so that inter-institutional comparisons can be made. In doing so, individual clinics will know if the calibration of their medical accelerator is within a normal range. These readings can be collected and analyzed automatically on a daily basis so that deviations are revealed in a timely way. Further, the integrated radiation detector 44 may be housed in a removable insert (i.e. removable support tube 42) that can be shipped to a centralized calibration facility and then repositioned in the device 10 with a high degree of reproducibility. Similarly, the camera or cameras 34 are embedded in the rigid inserts 36 that can be removed and replaced as necessary. In this manner the cameras 34 may be regarded as disposable device components and can be readily replaced. This mitigates concerns regarding any potential radiation damage to the performance of the cameras over time.

The calibrated light source 40 within the housing 12 functions to ensure the stability of the light intensity observed by the camera or cameras 34. This is done by comparing the measured light intensity to the known/calibration intensity so that any variations in the imaging system response can be corrected.

As a further benefit and advantage, the quality assurance device 10 is designed such that the light/radiation detecting camera or cameras 34 are stationary during all data collection. Other systems having cameras that are attached to the medical accelerator or that must be synchronously rotated with the accelerator gantry do not allow for the isolation of variables during data analysis as provided by the quality assurance device 10.

Advantageously, the CT image quality phantom 54 is coated on one side with a radioluminescent phosphor 56 that is visible by one or more of the cameras 34 within the housing 12. The intensity of light coming from the phosphor changes with the intensity of the radiation it receives. In this way, the CT image quality phantom 54 is able to acquire a full, two-dimensional picture of the radiation distribution, commonly referred to as "percent depth dose." The CT image quality phantom 54 also advantageously allows for measurement of electron beam characteristics. Further, the CT imaging phantom 54 may also have a diode, diodes and ionization chamber or ionization chambers or other detectors embedded within in order to assess the absolute radiation dose delivered to the device 10.

The foregoing has been presented for purposes of illustration and description. It is not intended to be exhaustive or to limit the embodiments to the precise form disclosed. Obvious modifications and variations are possible in light of the above teachings. For example, in the illustrated embodiment, the quality assurance device 10 includes three cameras 34. Substantially any number of cameras 34 from 1 to N may be provided. The illustrated embodiment of the quality assurance device 10 includes only one calibrated light source 40. More than one calibrated light source 40 may be provided if desired. There also may be more than one radiation detector 44 and more than one radiation dose detector 58.

As another example, the housing 12 of the illustrated embodiment is a cube-shape. The housing 12 may have another form or shape if desired. Further, the inner radioluminescent layer 26 of the quality assurance device 10 illustrated in the drawing Figures is also cube-shaped. That inner radioluminescent layer 26 may assume a different shape and may even assume a shape different from the outer layer 28 of the housing 12. All such modifications and variations are within the scope of the appended claims when interpreted in accordance with the breadth to which they are fairly, legally and equitably entitled.

What is claimed:

1. A quality assurance device for a medical accelerator, comprising:
    a housing having an inner radioluminescent layer adapted to provide a visual indication when contacted with invisible radiation generated by the medical accelerator;
    a radiation detector located within said housing;
    a calibrated light source located within said housing;
    at least one imaging test object carried on said housing wherein said at least one imaging test object includes a first group of imaging test objects positioned on a first side of said housing adapted to evaluate diagnostic, kV image quality including spatial resolution, contrast resolution and geometric integrity; and
    at least one camera, located within said housing, adapted to image the inner radioluminescent layer of said housing including the visual indication wherein said housing includes an outer layer of switchable material having a first state wherein visible light passes through said switchable material and a second state wherein visible light is at least partially obstructed from passing through said switchable material.

2. The quality assurance device of claim 1, wherein said at least one imaging test object includes a second group of imaging test objects positioned on a second side of said housing adapted to evaluate mega-voltage (MV) image quality of an electronic portal imaging device (EPID) of the medical accelerator including spatial resolution, contrast resolution and geometric integrity.

3. The quality assurance device of claim 2, wherein said at least one imaging test object includes a CT image quality phantom on a third side of said housing closest to an accelerator gantry of the medical accelerator when used for quality assurance testing.

4. The quality assurance device of claim 3, wherein said CT image quality phantom includes a radioluminescent phosphor on one side visible to said at least one camera.

5. The quality assurance device of claim 4, wherein said CT image quality phantom further includes a radiation dose detector.

6. The quality assurance device of claim 5, further including a plurality of receivers within said housing and said at least one camera is held on a first insert adapted to be releasably received by at least one of said plurality of receivers.

7. The quality assurance device of claim 6, wherein said radiation detector is held on a second insert adapted to be releasably received by at least one of said plurality of receivers.

8. The quality assurance device of claim 7, further including a computing device configured to convert light intensity detected by said at least one camera to radiation dose, convert light intensity detected by said at least one camera to radiation fluence, convert spatial location of the visual indication on the inner radioluminescent layer to a coordinate system that is defined relative to the medical accelerator, and compare locations of the radiation and radiation boundaries to the locations indicated by sources of visible light including room lasers, medical accelerator light field, and medical accelerator crosshairs.

9. A method of quality assurance for a medical accelerator, comprising:
  positioning a quality assurance device on a treatment couch of the medical accelerator; and
  detecting radiation delivered by the medical accelerator to the quality assurance device by producing a visual indication of the radiation on an inner layer of a housing of the quality assurance device and imaging that visual indication with at least one camera located within the housing of the quality assurance device.

10. The method of claim 9, further including switching a switchable material, on an outer layer of the housing, into a first state wherein visible light passes through the switchable material when the quality assurance device is positioned on the treatment couch and switching the switchable material into a second state wherein visible light is at least partially obstructed from passing through the switchable material when the radiation delivered by the medical accelerator is being detected.

* * * * *

UNITED STATES PATENT AND TRADEMARK OFFICE
CERTIFICATE OF CORRECTION

| | | |
|---|---|---|
| PATENT NO. | : 11,964,172 B2 | Page 1 of 1 |
| APPLICATION NO. | : 17/420659 | |
| DATED | : April 23, 2024 | |
| INVENTOR(S) | : Molloy et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 247 days.

Signed and Sealed this
Twenty-second Day of July, 2025

Coke Morgan Stewart
*Acting Director of the United States Patent and Trademark Office*